(12) United States Patent
Courtney et al.

(10) Patent No.: US 10,376,290 B2
(45) Date of Patent: *Aug. 13, 2019

(54) BONE PLATE AND PLATING SYSTEM FOR USE OF SAME

(71) Applicant: Eminent Spine LLC, Georgetown, TX (US)

(72) Inventors: Steve Courtney, Plano, TX (US); David Freehill, Temple, TX (US)

(73) Assignee: Eminent Spine LLC, Georgetown, TX (US)

( * ) Notice: Subject to any disclaimer, the term of this patent is extended or adjusted under 35 U.S.C. 154(b) by 1480 days.

This patent is subject to a terminal disclaimer.

(21) Appl. No.: 14/242,670

(22) Filed: Apr. 1, 2014

(65) Prior Publication Data

US 2014/0214093 A1 Jul. 31, 2014

Related U.S. Application Data

(63) Continuation of application No. 12/629,779, filed on Dec. 2, 2009, now Pat. No. 8,685,069.

(60) Provisional application No. 61/119,324, filed on Dec. 2, 2008.

(51) Int. Cl.
*A61B 17/80* (2006.01)
*A61B 17/86* (2006.01)
*A61B 17/70* (2006.01)

(52) U.S. Cl.
CPC ........ *A61B 17/7059* (2013.01); *A61B 17/809* (2013.01); *A61B 17/8052* (2013.01); *A61B 17/8057* (2013.01); *A61B 17/8061* (2013.01); *A61B 17/8605* (2013.01); *A61B 17/8066* (2013.01)

(58) Field of Classification Search
CPC ............ A61B 17/7059; A61B 17/8004; A61B 17/8014; A61B 17/8047; A61B 17/8052; A61B 17/8057; A61B 17/809; A61B 17/846; A61B 17/86; A61B 17/8605; A61B 2017/867; A61B 2017/8675
See application file for complete search history.

(56) References Cited

U.S. PATENT DOCUMENTS

| | | |
|---|---|---|
| 5,346,492 A | 9/1994 | Morgan |
| 6,942,665 B2 | 9/2005 | Gambale |
| 7,341,591 B2 | 3/2008 | Grinberg |
| 7,682,379 B2 | 3/2010 | Mathieu et al. |
| 7,914,561 B2 | 3/2011 | Konieczynski et al. |

(Continued)

OTHER PUBLICATIONS

ISR PCT/US2009/066449, Jan. 26, 2010.

*Primary Examiner* — David W Bates
(74) *Attorney, Agent, or Firm* — Scott T. Griggs; Griggs Bergen LLP

(57) ABSTRACT

A bone plate and plating system are for use of the same are disclosed. The bone plate includes a body having a span sufficient to overlap a portion of a bone. A screw hole extends through the body in order to receive a bone screw to attach for engaging the plate to the bone. The screw hole includes a counterbore having a beveled surface that intersects at a pinch point a bore having a conical surface of revolution that transitions into the bone engaging surface of the body. The beveled surface includes a variable geometry defining interleaved and rotationally-spaced contact and non-contact bone screw regions.

18 Claims, 5 Drawing Sheets

(56) References Cited

U.S. PATENT DOCUMENTS

| | | | |
|---|---|---|---|
| 8,685,069 B2* | 4/2014 | Courtney | A61B 17/7059 606/283 |
| 2003/0208205 A1 | 11/2003 | Gambale | |
| 2004/0260306 A1 | 12/2004 | Fallin et al. | |
| 2005/0085913 A1 | 4/2005 | Fraser et al. | |
| 2005/0187552 A1 | 8/2005 | Michelson | |
| 2006/0116683 A1 | 6/2006 | Barrall et al. | |
| 2006/0235400 A1 | 10/2006 | Schneider | |
| 2008/0234749 A1 | 9/2008 | Forstein | |
| 2009/0018588 A1 | 1/2009 | Eckhof et al. | |
| 2009/0143824 A1 | 6/2009 | Austin et al. | |
| 2009/0318977 A1 | 12/2009 | Di Giacomo et al. | |
| 2010/0312286 A1 | 12/2010 | Dell'Oca | |

* cited by examiner

BONE PLATE AND PLATING SYSTEM FOR USE OF SAME

PRIORITY STATEMENT & CROSS-REFERENCE TO RELATED APPLICATIONS

This application is a continuation of co-pending patent application Ser. No. 12/629,779 entitled "Bone Plate and Plating System for Use of Same," filed on Dec. 2, 2009, and issued Apr. 1, 2014, as U.S. Pat. No. 8,685,069 in the names of Steve Courtney and David Freehill; which claims priority from Ser. No. 61/119,324 entitled "Anterior Buttress Staple and Method for Use of Same" and filed on Dec. 2, 2008 in the names of Steve Courtney and David Freehill; which are hereby incorporated by reference for all purposes.

TECHNICAL FIELD OF THE INVENTION

This invention relates, in general, to medical implants useful for orthopedic surgeries and, in particular, to surgical bone plates and bone plating systems utilizing locking bone screws that fix the bone plate to an aspect of a bone to provide for stabilization thereof.

BACKGROUND OF THE INVENTION

Without limiting the scope of the invention, its background is described in connection with spinal implant stabilization of degenerated intervertebral discs, as an example. When an intervertebral disc is subject to degeneration caused by trauma, disease, and/or aging, for example, a partial or full removal from the spinal column is often required. This discectomy creates a void that may result in an alteration in the natural separation distance between adjacent vertebrae and an overall destabilization of the spinal column. To maintain the natural separation between the vertebrae and to help prevent pressure from being applied to nerves that pass between vertebral bodies, an intervertebral spinal implant is inserted within the space created by the removal or partial removal of an intervertebral disc between adjacent vertebrae. The spinal implant may maintain the height of the spine and restore stability to the spine. Later and in some instances, intervertebral bone growth may fuse the spinal implant to adjacent vertebrae.

The spinal implant may be inserted during a spinal fixation procedure using an anterior, lateral, or posterior spinal approach. In some situations, the anterior approach results in an easier approach, less muscle and tissue damage, and/or less bone removal than other approaches. Following insertion of the spinal implant, a spinal plate is coupled to one or more vertebrae in order to stabilize the vertebrae and inhibit backout of the spinal implant from between vertebrae.

Fasteners (e.g., bone screws) may be used to fasten the spinal plate to vertebrae. There exists a continuing need for spinal plates that inhibit backout while causing minimum damage to the surrounding bone and tissue during implantation as well as subsequent use following implantation.

SUMMARY OF THE INVENTION

A bone plate and plating system, with locking screw, for use of the same are disclosed. The bone plate includes a body having a span sufficient to overlap a portion of a bone. A screw hole extends through the body in order to receive a bone screw to attach for engaging the plate to the bone. The screw hole includes a counterbore having a beveled surface that intersects at a pinch point a bore having a conical surface of revolution that transitions into the bone engaging surface of the body. The beveled surface includes a variable geometry defining interleaved and rotationally-spaced contact and non-contact bone screw regions.

In the plating system utilizing the bone plate, a screw is employed to be inserted into the bone. The screw includes a head region configured to be secured within the screw hole and an elongated body threaded extending therefrom to a distal end of the screw. The screw also includes a proximal root portion at the head region that furnishes a sloping radial surface ending in a continuous rib which radially projects from the screw. The pinch point of the screw hole flexibly captures the screw to limit axial travel by a detented engagement between the pinch point and a junction of the sloping radial surface and the continuous rib.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 5 is a side elevation view of one embodiment of a screw for use with the bone plating system depicted in FIG. 1;

FIG. 11 is a top plan view of another embodiment of a bone plate according to the teachings presented herein;

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figure 1:
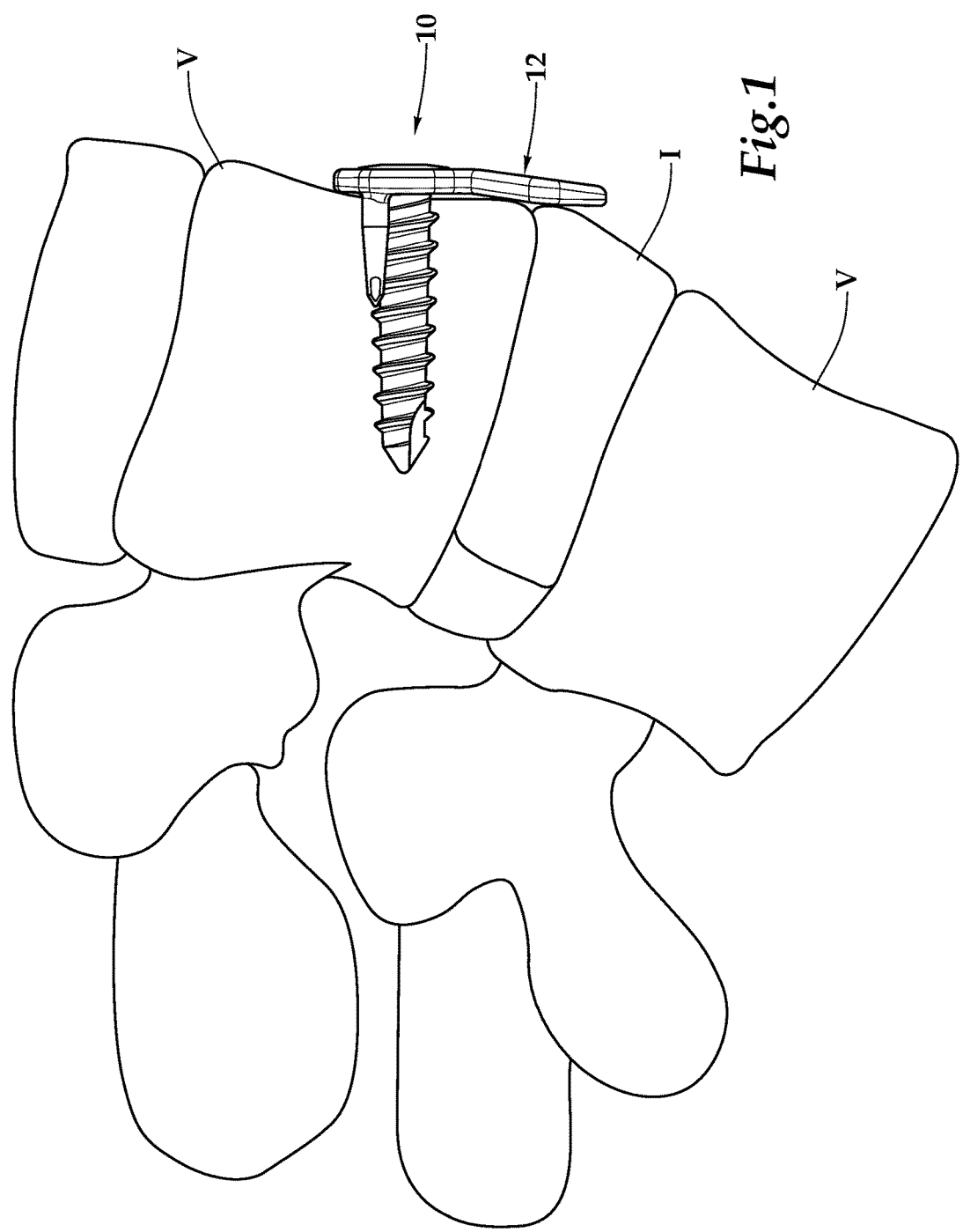
FIG. 1 is an illustrated view of one embodiment of a bone plating system implanted into a human vertebral column.
Figure 2:
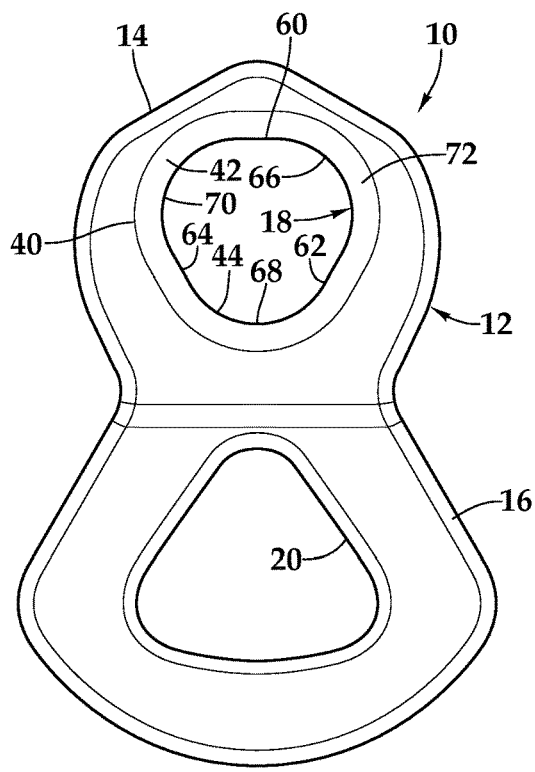
FIG. 2 is a top plan view of one embodiment of a bone plate which forms a portion of the bone plating system depicted in FIG. 1.
Figure 3:
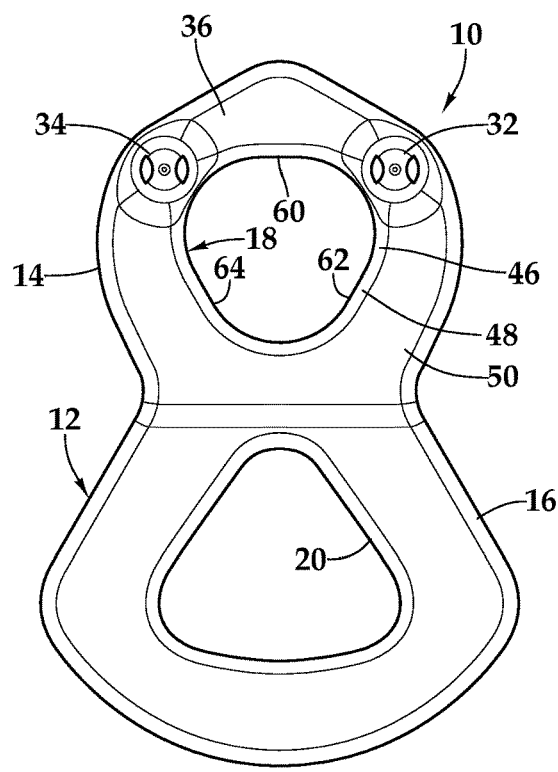
FIG. 3 is a bottom plan view of the bone plate depicted in FIG. 2.
Figure 4:
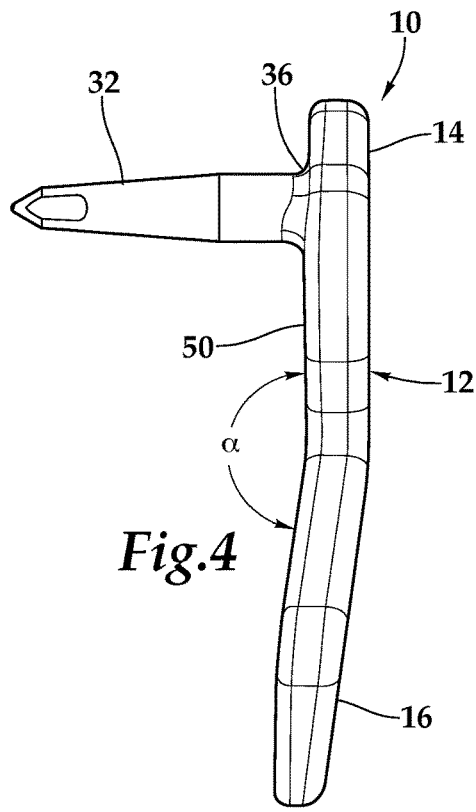
FIG. 4 is a side elevation view of the bone plate depicted in FIG. 2.
Figure 6:
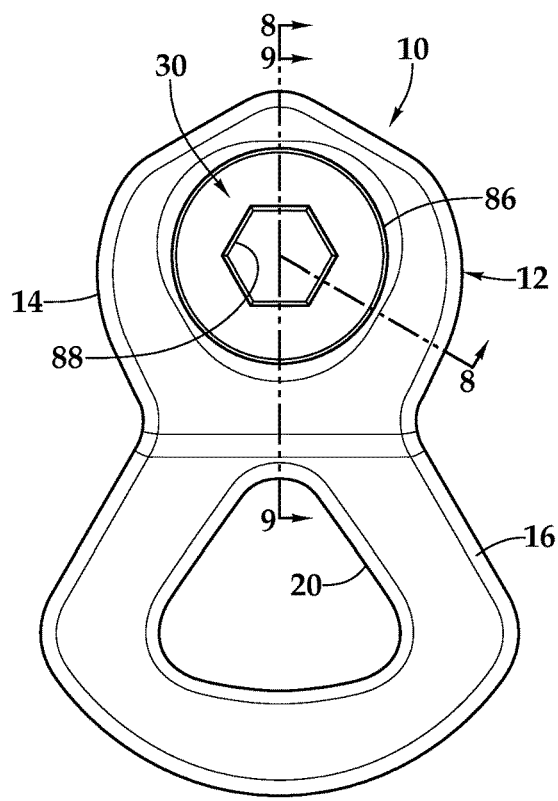
FIG. 6 is a top plan view of the bone plating system depicted in FIG. 1.
Figure 7:
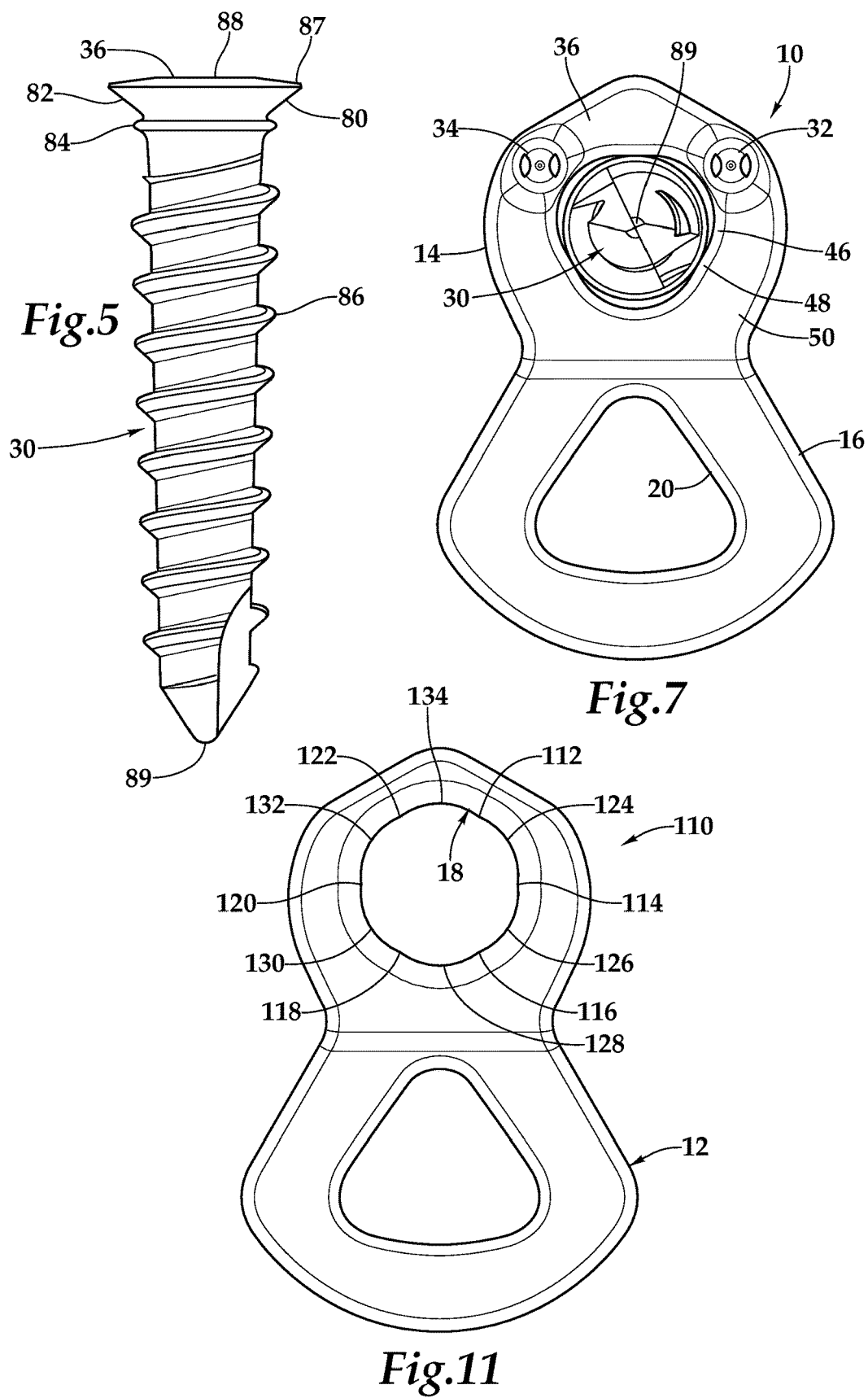
FIG. 7 is a bottom plan view of the bone plating system depicted in FIG. 1.

Referring to FIG. 1, therein is depicted a bone plating system 10, which for purposes of explanation, is depicted as including a bone plate that is schematically illustrated and generally designated 12 and shown as an anterior buttress staple or buttress plate. A bone plate may be a relatively thin metal device which is affixed to bone via screws, such as screw, which, in one implementation, may be any threaded device of metal or other material(s) which is inserted into bone. The bone plate may be used to immobilize bones or bone fragments such that healing can occur. In this respect, the bone screw engages bones in order to immobilize bones or bone fragments or to affix other medical devices, such as metal bone plates, to bones. In particular, the bone plate or the buttress plate 12 in the form of a spinal plate is utilized to support the internal stabilization of adjacent vertebral bodies of a spinal column after replacement of an intervertebral disk, for example. As shown, in one operational embodiment, following insertion of a spinal implant I between vertebrae V, the bone plate 12 is coupled to vertebra V in order to stabilize the vertebrae V and inhibit backout of the spinal implant I from between vertebrae V.

Figure 8:
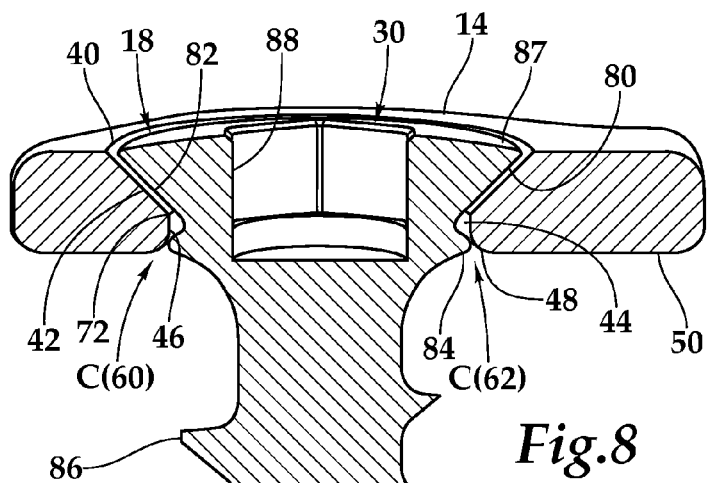
FIG. 8 is a cross-sectional view of a portion of the bone plating system depicted in FIG. 1 along a 120° section as shown in line 8-8 of FIG. 6 to illustrate a locking mechanism.

Referring now to FIG. 2 through FIG. 7, the bone plate 12 includes a "figure 8" shaped body having upper and lower body portions 14, 16 each including openings that respectively provide a screw hole 18 and a visualization window 20. The lower body portion 16 further includes a broad span that prevents graft expulsion during use. Additionally, an angle of displacement a between the upper body portion 14 and the lower body portion 16 is present to reflect angle of lordosis, such as an angle of cervical lordosis.

The screw hole 18 located at the upper body portion 14 and extending therethrough from an upper surface to a lower surface accepts a self tapping screw 30 that is threaded into one of the vertebral bodies, thereby securing the buttress plate 12 and extending the lower body portion 16 over the replaced intervertebral disk. A pair of fangs 32, 34, which provide rotational stability, are located along a lip 36 of the upper body portion 14 and are equally spaced about the screw hole 18. The pair of fangs 32, 34 cooperate with the self tapping screw 30 to furnish a tripod fixation.

The screw hole 18 includes a counterbore 40 having a beveled surface 42 that intersects, at a pinch point 44, a bore 46 having a conical surface of revolution 48 that transitions into a bone contacting surface 50 of the buttress plate 12. It should be appreciated that the surface of revolution 48 may be of a geometry or curvature other than a conical surface. The counterbore 40 includes three substantially equally rotationally spaced contact regions 60, 62, 64 that align with the sides of an equilateral triangle. Three non-contact regions 66, 68, 70 include three substantially equally rotationally spaced regions that align with a non-linear cross-section of a cylinder. The contact regions 60-64 and non-contact regions 66-70 alternate to form a varied surface 72 (See FIGS. 8-10), which has 60°, 120°, 180°, and 240° rotational symmetry and three mirror planes of symmetry.

With respect to the screw 30, the screw 30 is configured to be inserted into bone. A head region 87 includes a proximal root portion 80 which is configured to be secured within the screw hole 18 and an elongated body extends therefrom to a distal end having a point 89. The elongated body may be a threaded as shown by threaded elongated body 86, in order that the engagement of the bone is made stronger. The proximal root portion 80 has a sloping radial surface 82 ending in a continuous rib 84 which radially projects from the screw. The sloping radial surface 82 conforms to the shape of the counterbore 40. The screw 30 further includes a socket 88 in the head region 87 in one implementation.

During a spinal fixation procedure wherein the bone plate 12 has the form of an anterior buttress staple, the bone plating system 10 is utilized following the removal of the intervertebral disc and the insertion of a spinal implant to stabilize the spinal column. The bone plate 12 is positioned along the spinal column proximate to the spinal implant to act like a bracket, urging against the spinal implant to prevent the expulsion of the spinal implant from the spinal column. The pair of fangs 32, 34 are tapped into the bone to hold the bone plate 10 in position such that the lower body portion 16 spans across the spinal implant. As previously mentioned, the visualization window 20 in the lower body portion 16 assists with the placement of the anterior buttress staple 10. Additionally, the pair of fangs 32, 34 provide for bipod support that transitions into tripod support with the insertion of the screw 30.

The screw 30, which may be a self taping screw, is inserted into the bone through the screw hole 18 which is configured to expand and contract to alleviate stress and torque during implantation. The pinch point 44 provides an interference fit between the screw 30 and the bone plate 12. More particularly, the pinch point 44 flexibly captures the screw 30 to limit axial travel by a detented engagement between the pinch point 44 and the junction of the sloping radial surface 82 and rib 84. The screw hole 18 and the visualization window 20 of the anterior buttress plate distribute the compressive and torque loads applied to the spinal implant or spinal implants inserted between vertebrae. Accordingly, the bone plating system 10 furnishes a stabilization plate that provides a secured-locking mechanism for fixation of an intervertebral disk and a measure of flexibility following implantation as well.

Figure 10:
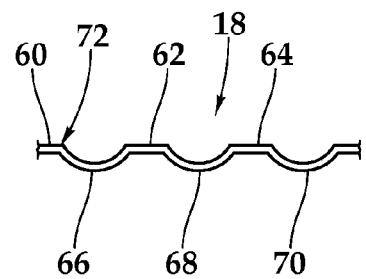
FIG. 10 is a two-dimensional representation of a portion a three-dimensional screw hole depicted in FIGS. 8 and 9.
Figure 9:
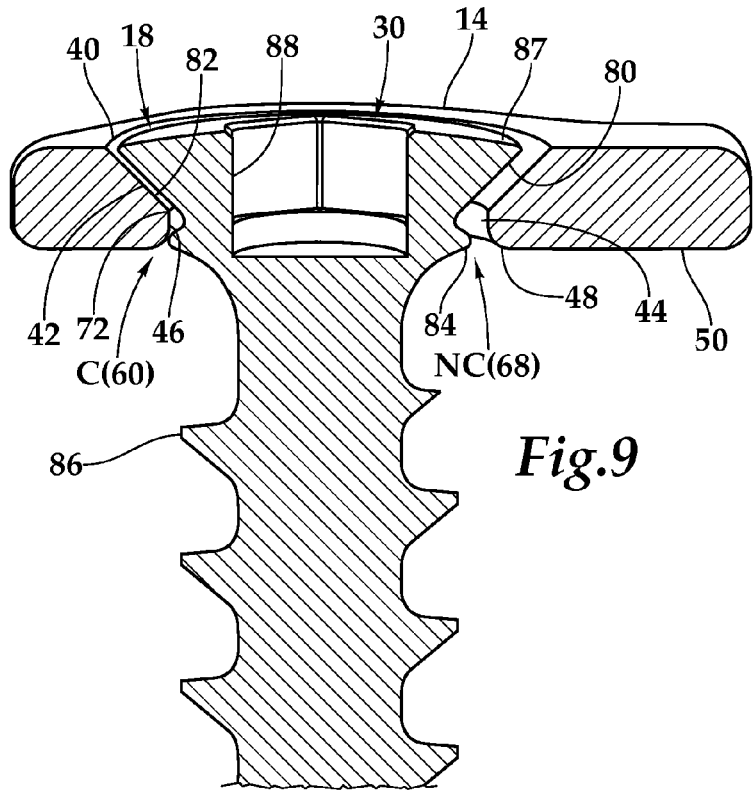
FIG. 9 is a cross-sectional view of a portion of the bone plating system depicted in FIG. 1 along a 180° section as shown in line 9-9 of FIG. 6 to illustrate the locking mechanism.

With reference to FIG. 8 through FIG. 10, the varied opening 72 of the screw hole 18 may be a resilient, flexible opening that provides for the removal of the bone plate 10 during revision surgery when the bone plate 10 is required to be lifted or otherwise removed from the bone. The non-contact regions 66-70 provide space between the screw 30 and anterior buttress staple 10 for the manipulation and/or application of leverage to the screw 30 to assist with the removal of the screw 30 and anterior buttress staple. The contact and non-contact aspects of the varied opening 72 are presented in FIG. 8 and FIG. 9, wherein in FIG. 8 (NB, non-180° cross-section), screw contact, as represented by the letter C, is made with contact region 60 and contact region 62. In FIG. 9, however, at the same time as shown by the 180° cross-section, contact is made with contact region 60 and no screw contact, as represented by the letters NC, is made with non-contact region 68.

More particularly, the varied opening 72, which is depicted as a continuous surface, provides a variable geometry (See FIG. 10) defining interleaved and rotationally-spaced contact and non-contact bone screw regions. In one embodiment, the varied opening 72 may oscillate or alternate between providing contact surfaces (e.g., non-contact regions 66-70) or contact planes and areas of non-contact which are regions disposed in a non-coplanar relationship with the contact planes. The varied opening 72 may be, as mentioned, a continuous surface, an uninterrupted surface, or a continuous, uninterrupted surface, for example.

The screw hole 18 may include any combination of contact and non-contact regions and the number and placement of contact and non-contact regions are not limited to the previous presentations, wherein three of each were depicted and described. Any number of non-contact regions may be interleaved with any number of contact regions to create the continuous surface. FIG. 11 depicts such an embodiment of bone plate 110. In this implementation, contact regions 112, 114, 116, 118, 120, 122 are separated by non-contact regions, which include non-contact regions 124, 126, 128, 130, 132, 134.

Moreover, the screw hole 18 is not limited to anterior buttress staples, but may be utilized with other types of surgical implant plates as well regardless of location of installation in the body. That is, the bone plate 12 may take any form and the body may be shaped to conform to any type of bone including, for example, spinal vertebrae, cranium, maxilla, mandible, clavicle, humerus, acromion, ulna, radius, tarsal, metatarsal, phalange, carpal, metacarpal, ilium, pubic, femur, tibia, fibula, calcaneus, talus, navicular, or cuboid. The bone plate 12 may vary in structure depending on application and, for example, the lower surface may be concave along a substantial portion of a longitudinal access of the body. Moreover, the bone plate 12 may be used in combination with an interbody implant, a bone graft, or a bone growth promoting material, for example.

Figure 12:
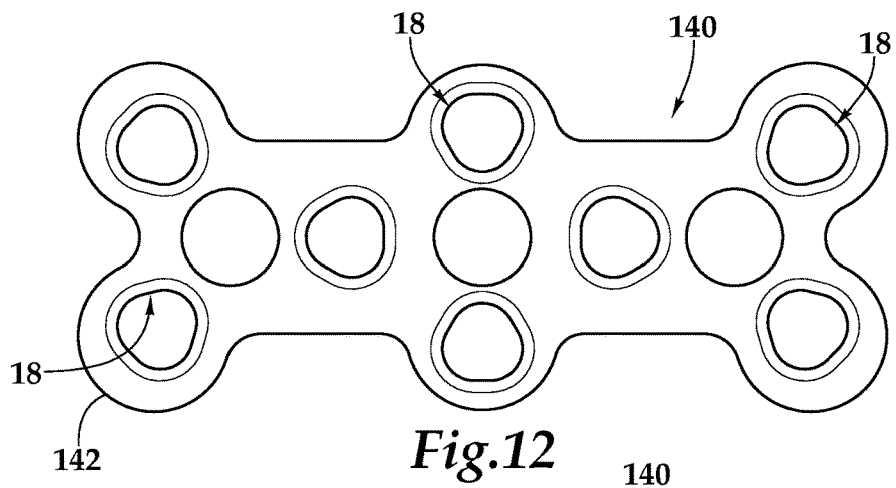
FIG. 12 is a top plan view of a further embodiment of a bone plate according to the teachings presented herein.
Figure 13:
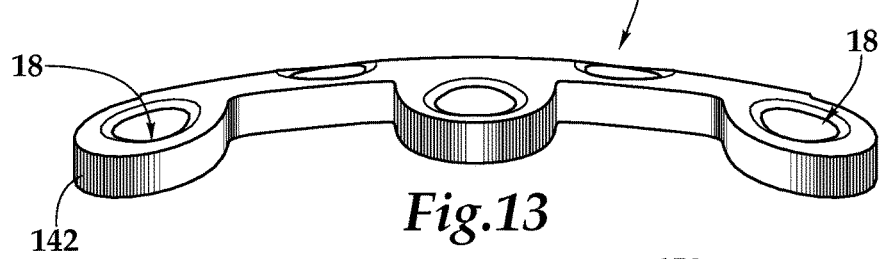
FIG. 13 is a side elevation view of the bone plate depicted in FIG. 12.

By way of example, FIGS. 12 and 13 depict an anatomically contoured cervical plate with bone ingrowth surfaces, providing for intersegmental compressive preloading, and a rigid and locked interface to all of the bone screws by way of screw holes 18. Moreover, as shown, the bone plate 140 may be concave along a substantial portion of a longitudinal access of the body 142.

In this embodiment, similar to the previous embodiments, the bone plate 140 includes a body 142 having a thickness and a span sufficient to overlap a portion of a bone. A lower surface of the bone plate is for placement against the bone and an upper surface is opposite the lower surface. The screw hole 18 extends through the body from the upper surface through the lower surface. The screw hole 18 is adapted to receive a bone screw to attach for engaging the bone plate 140 to the bone and may be a resilient aperture. The screw hole 18 includes a counterbore having a beveled surface that intersects at a pinch point a bore having a conical surface of revolution that transitions into the lower surface. In this embodiment, the varied opening and beveled surface of the screw hole 18 include a variable geometry defining interleaved and rotationally-spaced contact and non-contact bone screw regions. As shown, additional screw holes 18 may be utilized in the bone plate.

Figure 14:
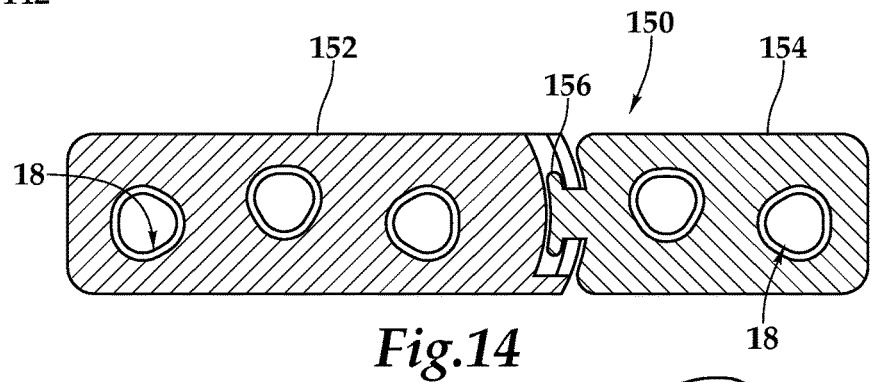
FIG. 14 is a top plan view of a still further embodiment of a bone plate according to the teachings presented herein.

Byway of another example, a bone plate may have a span that is sufficient to overlap a portion of a second bone in addition to the first bone. FIG. 14 depicts a bone plate 150 having plate portions 152, 154 hingedly connected at hinge 156. The bone plate 150 includes screw holes 18 and joins the fracture of a pelvis. The plate portions 152, 154 are placed on either side of the fracture and secured to the bone by way of screws and screw holes 18.

Figure 15:
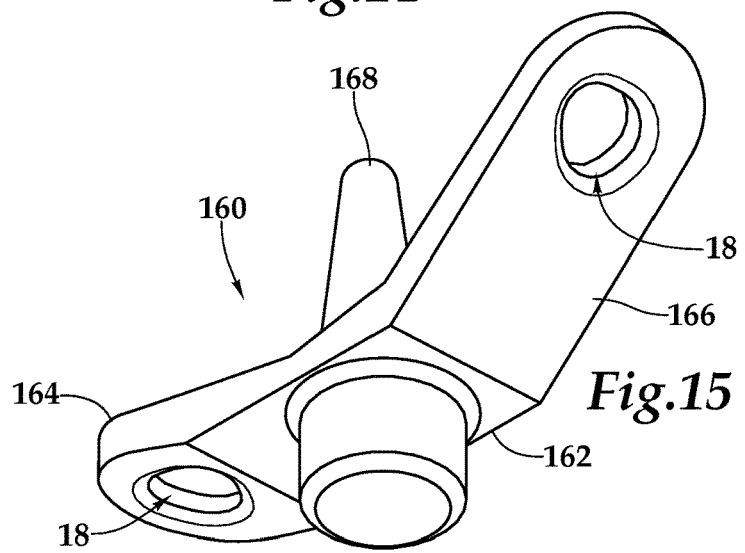
FIG. 15 is a front perspective view of an additional embodiment of a bone plate according to the teachings presented herein.

To further illustrate that the embodiments of the bone plate including the screw hole 18 may be used in other plating applications, as previously mentioned, FIG. 15 is presented wherein a bond plate 160 defines a prosthetic wrist having a radial insert, which is configured to be fixed to the resected radius of a patient by way of a body 162 having a carpal implant 168 and wrist bearing components 164, 166. In this bone plate implementation, screw holes 18 are located on the bearing components 164, 168.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A bone plating system adapted for contacting at least a portion of a bone, the plating system comprising:
   a plate including a body having a span sufficient to overlap a portion of the bone, the body having a lower surface for placement against the bone and an upper surface opposite the lower surface;
   a screw hole extending through the body from the upper surface through the lower surface, the screw hole being adapted to receive a bone screw to attach for engaging the plate to the bone;
   wherein the screw hole includes a counterbore having a beveled surface that intersects at a pinch point a bore having a conical surface of revolution that transitions into the lower surface;
   wherein the beveled surface has a variable geometry defining alternating linear contact bone screw regions and arcuate non-contact bone screw regions that are interleaved and rotationally-spaced;
   wherein the beveled surface comprises an uninterrupted, circumferentially continuous surface;
   a screw configured to be inserted into the bone, the screw having a head region configured to be secured within the screw hole and an elongated body extending therefrom to a distal end of the screw, the elongated body including a threaded portion for engaging the bone;
   wherein the screw includes a proximal root portion of the head region, the proximal root portion having a sloping radial surface ending in a continuous rib which radially projects from the screw; and
   wherein the pinch point flexibly captures the screw to limit axial travel by a detented engagement between the pinch point and a junction of the sloping radial surface and the continuous rib.

2. The plating system as recited in claim 1, wherein the screw hole comprises a resilient aperture.

3. The plating system as recited in claim 1, wherein the span is sufficient to overlap a portion of a second bone.

4. The plating system as recited in claim 1, further comprising at least one additional screw hole extending through the body.

5. The plating system as recited in claim 1, wherein the lower surface is concave along a substantial portion of a longitudinal access of the body.

6. The plating system as recited in claim 1, in combination with an interbody implant.

7. The plating system as recited in claim 1, in combination with a bone graft.

8. The plating system as recited in claim 1, in combination with a bone growth promoting material.

9. The plating system as recited in claim 1, wherein the body is shaped to conform to a bone selected from the group consisting of spinal vertebrae, cranium, maxilla, mandible, clavicle, humerus, acromion, ulna, radius, tarsal, metatarsal, phalange, carpal, metacarpal, ilium, pubic, femur, tibia, fibula, calcaneus, talus, navicular, and cuboid.

10. A bone plating system adapted for contacting at least a portion of a bone, the plating system comprising:

a plate including a body having a span sufficient to overlap adjacent vertebral bodies of a spinal column, the body having a lower surface for placement against the bone and an upper surface opposite the lower surface, the body including a figure-8-shape having first and second body portions;

a screw hole extending through the first body portion from the upper surface through the lower surface, the screw hole being adapted to receive a bone screw to attach for engaging the plate to the bone;

wherein the screw hole includes a counterbore having a beveled surface that intersects at a pinch point a bore having a conical surface of revolution that transitions into the lower surface;

wherein the beveled surface has a variable geometry defining alternating linear contact bone screw regions and arcuate non-contact bone screw regions that are interleaved and rotationally-spaced;

wherein the beveled surface comprises an uninterrupted, circumferentially continuous surface;

a window extending through the second body portion from the upper surface through the lower surface, the window being adapted to provide for visualization of a portion of the adjacent vertebral bodies; and a pair of fangs coupled to the lower surface of the first body portion, the pair of fangs being equally spaced about the screw hole, the pair of fangs for engaging the bone to provide rotational stability;

a screw configured to be inserted into the bone of one of the vertebral bodies, the screw having a head region configured to be secured within the screw hole and an elongated body extending therefrom to a distal end of the screw, the elongated body including a threaded portion for engaging the bone;

wherein the screw includes a proximal root portion of the head region, the proximal root portion having a sloping radial surface ending in a continuous rib which radially projects from the screw; and wherein the pinch point flexibly captures the screw to limit axial travel by a detented engagement between the pinch point and a junction of the sloping radial surface and the continuous rib.

11. The plating system as recited in claim 10, wherein the body comprises a plurality of screw holes.

12. The plating system as recited in claim 10, wherein an angle of displacement between the first body portion and the second body portion is present to reflect angle of lordosis, including an angle of cervical lordosis.

13. The plating system as recited in claim 10, wherein the pair of fangs cooperate with the screw to furnish a tripod fixation.

14. A bone plate adapted for contacting at least a portion of a bone, the bone plate comprising:

a plate including a body having a span sufficient to overlap a portion of the bone, the body having a lower surface for placement against the bone and an upper surface opposite the lower surface;

a screw hole extending through the body from the upper surface through the lower surface, the screw hole being adapted to receive a bone screw to attach for engaging the plate to the bone;

wherein the screw hole includes a counterbore having a beveled surface that intersects at a pinch point a bore having a conical surface of revolution that transitions into the lower surface;

wherein the beveled surface has a variable geometry defining three linear contact bone screw regions and three arcuate non-contact bone screw regions that are interleaved and rotationally-spaced;

wherein the beveled surface comprises an uninterrupted, circumferentially continuous surface; and wherein the pinch point is configured to flexibly capture a screw to limit axial travel by a detented engagement between the pinch point and the screw.

15. The bone plate as recited in claim 14, wherein the screw hole comprises a resilient aperture.

16. The bone plate as recited in claim 14, wherein the span is sufficient to overlap a portion of a second bone.

17. The bone plate as recited in claim 14, further comprising at least one additional screw hole extending through the body.

18. The bone plate as recited in claim 14, wherein the lower surface is concave along a substantial portion of a longitudinal access of the body.

* * * * *